United States Patent [19]

Lee

[11] Patent Number: 5,325,709

[45] Date of Patent: Jul. 5, 1994

[54] MEASUREMENT, CALIBRATION AND PROBE STORAGE APPARATUS FOR MEASURING PH OF FLUIDS AND SLURRIES

[75] Inventor: C. Lynden Lee, Duncan, Okla.

[73] Assignee: Halliburton Company, Duncan, Okla.

[21] Appl. No.: 4,324

[22] Filed: Jan. 14, 1993

[51] Int. Cl.⁵ .................... G01N 33/00; G01N 11/00
[52] U.S. Cl. .................... 73/61.43; 73/53.01; 73/1 R; 73/19.1; 422/68.1; 422/82.03; 436/29
[58] Field of Search ................ 73/53.01, 61.41, 61.43, 73/61.44, 151, 151.5, 1 R, 19.09, 19.1; 422/68.1, 82.03; 166/40, 48, 250; 436/29

[56] References Cited

U.S. PATENT DOCUMENTS

| | | | |
|---|---|---|---|
| 3,025,464 | 3/1962 | Bond | 73/53.01 X |
| 3,115,776 | 12/1963 | Green | 73/155 |
| 3,214,964 | 11/1965 | Davis | 73/53.01 |
| 3,763,422 | 10/1973 | MacPhee et al. | 422/82.03 X |
| 3,765,226 | 10/1973 | Strickland et al. | 73/53.01 X |
| 4,668,346 | 5/1987 | Entwistle | 422/82.03 |
| 4,905,510 | 3/1990 | Brickhouse | 73/155 |
| 4,949,572 | 8/1990 | Wilen et al. | 73/53.01 |

Primary Examiner—James C. Housel
Assistant Examiner—Milton I. Cano
Attorney, Agent, or Firm—Stephen R. Christian

[57] ABSTRACT

A measurement/calibration/probe storage apparatus particularly suitable for measuring pH of fluids and slurries used in the treatment of oil and gas wells. The apparatus includes an enclosure having a conduit for the conveyance of a fluid or slurry therein, a flow chamber being in fluid communication with the conduit, a probe sensor for measuring a preselected attribute of a fluid, or slurry, residing within, or passing through the flow chamber. The apparatus further includes an electronic processor in electrical communication with the probe sensor for calculating and providing a display of the attribute being measured and a calibration chamber being configured to receive the probe sensor. At least one calibration fluid container being in fluid communication with the calibration chamber is also provided. A control valve is provided for controlling the flow of fluid from each calibration fluid container into the calibration chamber and for controlling the draining of the calibration chamber.

12 Claims, 3 Drawing Sheets

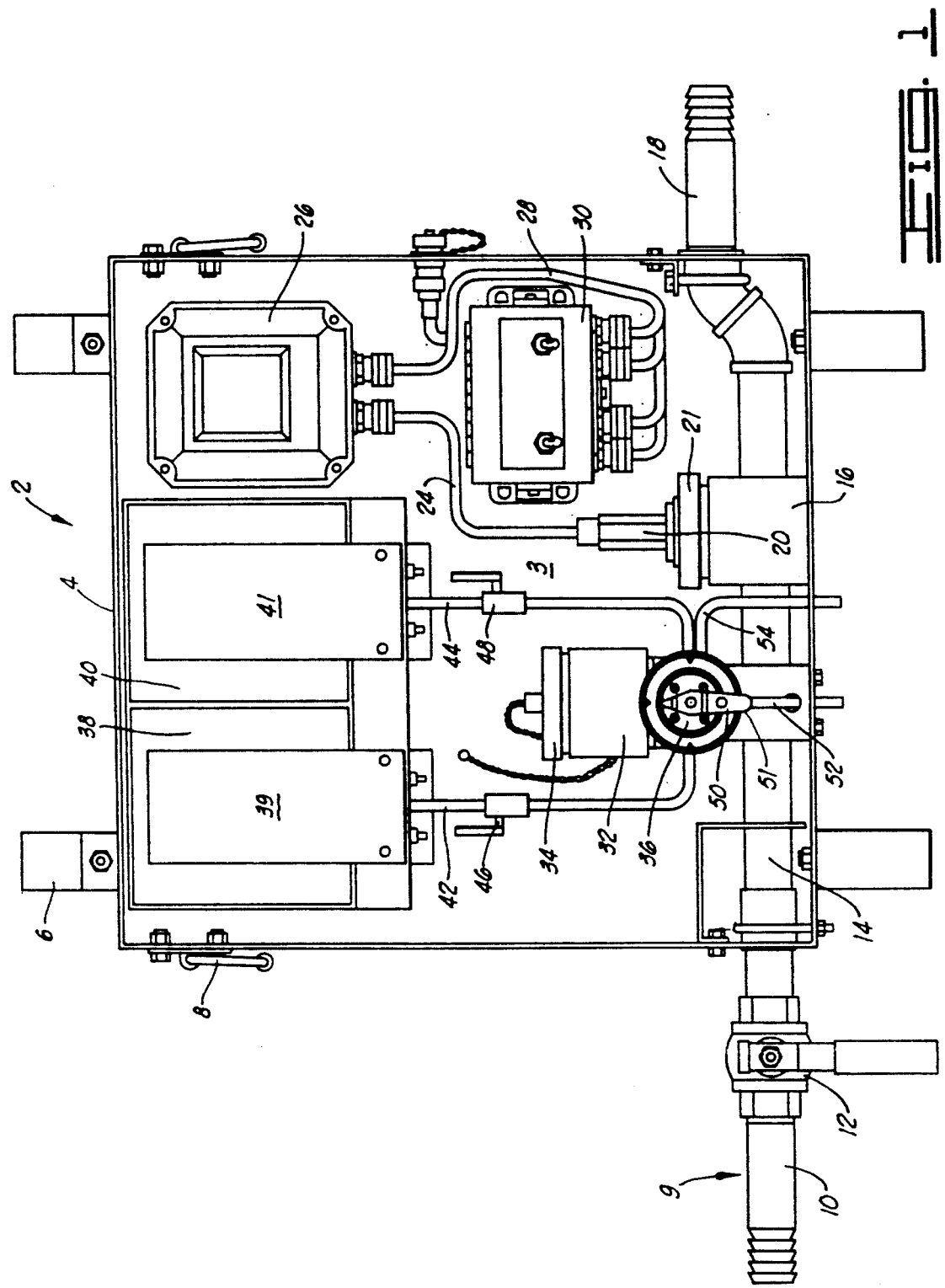

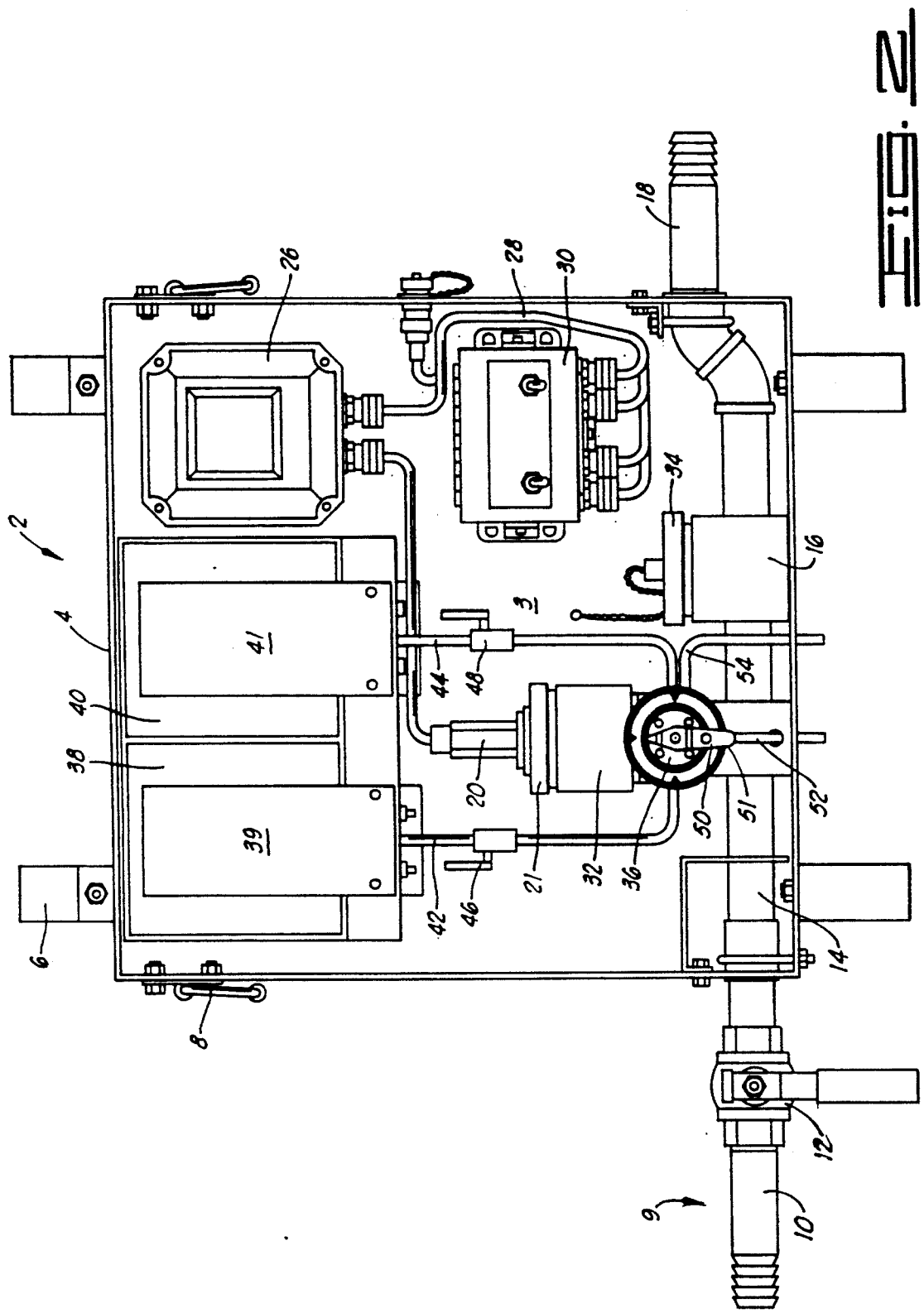

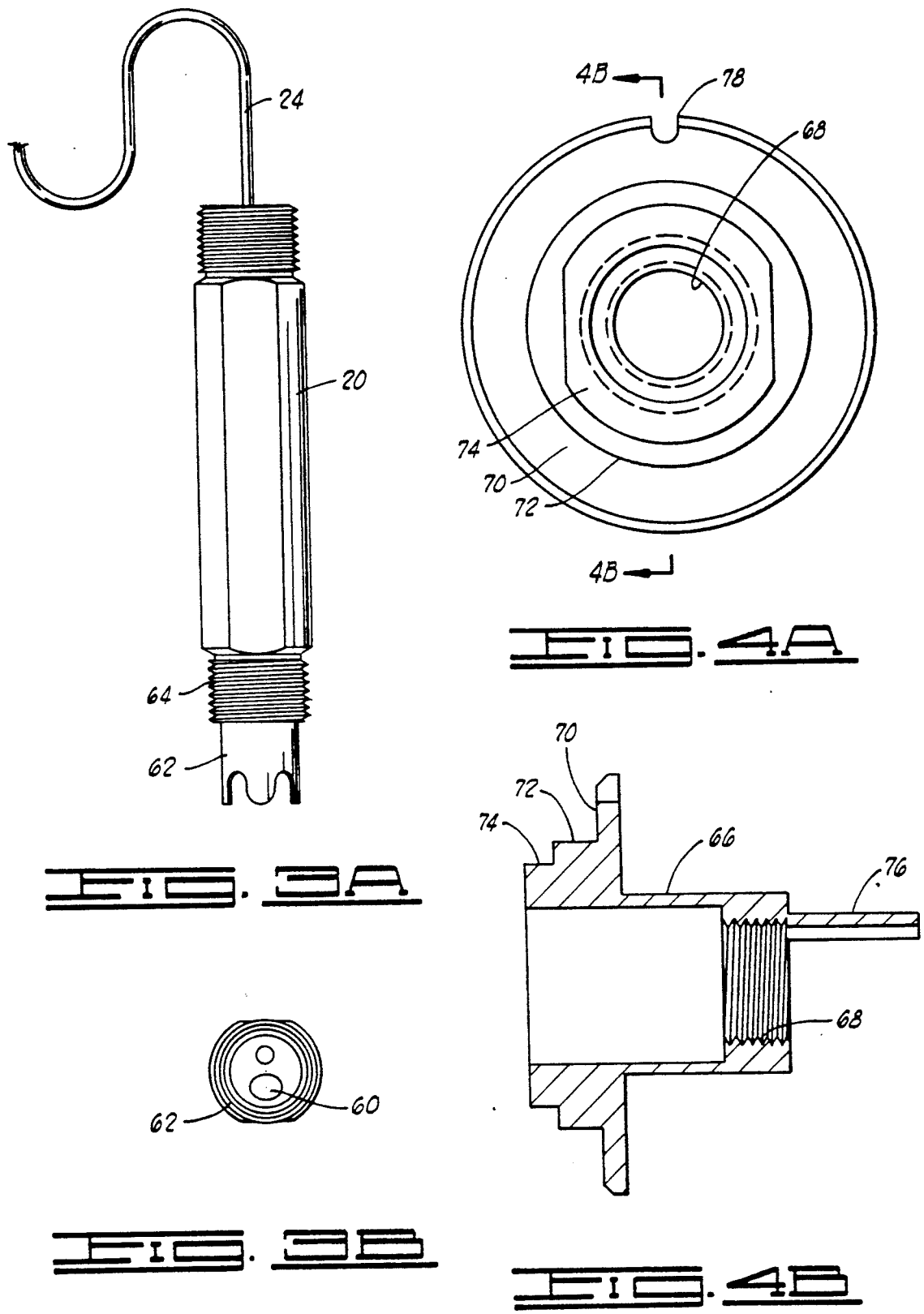

MEASUREMENT, CALIBRATION AND PROBE STORAGE APPARATUS FOR MEASURING PH OF FLUIDS AND SLURRIES

BACKGROUND OF THE INVENTION

This invention relates generally to measuring preselected attributes of process fluids and slurries. More specifically, this invention is particularly suitable for, but not limited to, the in-line measurement and monitoring of the pH of fluids and slurries used in oil field operations.

Currently, various oil field services require that liquids and slurries that are to be injected into the well bore have pH values within a specific pH range. Furthermore, as well-treatments become more complex, it is becoming essential that the formulated liquids and slurries to be used in the treatment have a pH within a very narrow range to ensure the successful treatment of the well. Thus, pH measuring of liquids and slurries must be accurate, reliable, and to ensure the best results, capable of being performed while the liquids and slurries are being pumped into, or about the well.

Historically, the pH of a liquid, or slurry, has been monitored by obtaining a sample of the liquid, or slurry, and submerging a pH indication tape or an electronic probe sensor into the sample. In the case of using a probe, the probe generates an electrical signal that is converted into meaningful pH values by an appropriate electronic processor and those values are displayed on a meter, charted, or otherwise recorded. In order to calibrate the probe sensor, at least one, and preferably two buffer solutions having known but different pHs must be kept on hand. The probe sensor calibration process includes checking and tuning the electronic processor to display the desired value for each buffer solution. For example, if a selected calibration solution has a pH of 7, the processor would be adjusted to display the value of 7 indicating a neutral pH. The probe sensor could then be subjected to a second buffer solution having a different pH and the processor again adjusted to display the correct value. The calibration steps are repeated as necessary to ensure that the monitoring system is properly calibrated. Additionally, the probe sensor, when not in use, must be kept submerged in an aqueous solution to prevent the sensor from drying and thus permanently damaging the probe sensor.

The above procedures are not difficult to perform in a laboratory environment, however, the procedures can be very difficult to perform in conditions typically found in the field, such as extreme heat and cold, high winds, dust, rain, and snow, etc.

Therefore, there remains a need within the art for measuring/calibration/probe storage apparatus that provides an effective and convenient system to measure selected attributes of liquids and slurries, such as the pH thereof, in adverse conditions as well as a need for an apparatus that provides a means for storing probes for extended periods of time in such conditions.

There also remains a need within the art for measuring/calibration/probe storage apparatus that is capable of measuring selected attributes such as the pH of a liquid, or slurry, while such liquid, or slurry is in transit to the well bore, often referred to as being "on-line".

There is a further need within the art for measuring/calibration/probe storage apparatus which allows for the calibration and installation of a replacement probe without disturbing the well treatment operation.

These and other needs within the art are met by the invention disclosed herein.

SUMMARY OF THE INVENTION

The present invention provides a measuring/calibration/probe storage apparatus having an enclosure having a conduit located therein. An optional shutoff valve may be provided in the conduit. A flow chamber is installed in fluid communication at an intermediate location along the conduit. The flow chamber is configured to receive a removable probe sensor therein for measuring a preselected attribute of a fluid passing through, or, residing within the flow chamber. The probe sensor is in electrical communication with electronic processor means for calculating and providing a display of the attribute being measured. A calibration chamber having a removable cover is positioned within proximity of the flow chamber. At least one buffer fluid container is provided which is in fluid communication with the calibration chamber. Preferably a valve for controlling the flow of fluid from each container into the calibration chamber is provided. The calibration chamber is further provided with a valve means for selectively allowing the filling or draining of the calibration chamber. The apparatus preferably further comprises a shielding means for protecting the sensor portion of the probe from abrasives contained within the fluid, or slurry, being monitored.

An important object of the disclosed invention is to provide an apparatus that is particularly suited to being connected to fluid blending equipment at a well-site for accurately and reliably measuring the pH of the fluid blend while on-line.

Another important object of the disclosed invention is to provide an apparatus that allows for the calibration and installation of a probe sensor without disturbing the well treatment operation.

A further important object of the disclosed invention is to provide an apparatus for protective storage of probe sensors in an aqueous solution for long periods of time in harsh environments such as those commonly encountered at well-sites and at equipment storage areas.

Another important object of the disclosed invention is to provide a probe having a shield to protect a sensor installed therein from being prematurely destroyed by sand or other abrasives within the fluid, or slurry, being monitored.

Additional objects and advantages of the disclosed invention will become apparent in light of the drawings and the detailed description of the preferred embodiment.

BRIEF DESCRIPTION OF THE DRAWINGS

FIG. 1 is a front view of the preferred embodiment of the subject apparatus having the front panel of the protective enclosure removed and wherein the sensor probe is shown installed in the flow chamber.

FIG. 2 is the same view provided in FIG. 1 with the exception that the probe sensor is shown installed in the calibration chamber.

FIG. 3A is a front view of the sensor probe body having a sensor installed therein.

FIG. 3B is a bottom view of the sensor probe body.

FIG. 4A is a top view of the probe sensor retainer/shield.

FIG. 4B is a cross-sectional view of the probe sensor retainer/shield taken along line 4B depicted in FIG. 4A.

DETAILED DESCRIPTION OF THE PREFERRED EMBODIMENT

Referring now to FIG. 1 of the drawings, a front view of the preferred embodiment of a measurement-/calibration/probe storage apparatus 2 is shown. Apparatus 2 includes a protective enclosure 4 made of steel sheet or other suitable material. Enclosure 4 is preferably rectangular shaped and has a hinged front access panel (not shown in the drawings), a back panel, top and bottom panels, and side panels. Mounting tabs 6 provide a convenient means of mounting enclosure 4 at a suitable location at the well-site. Handles 8 provide a convenient means for grasping the enclosure for transport. The subject apparatus however, may be protected by full enclosures having other geometries, partial enclosures, or the apparatus may be assembled upon a single panel for example, without the benefit of being fully enclosed and thus protected from the environment.

Fluid line or conduit 9 having an inlet section 10 is introduced to the interior of the enclosure at a preselected position. A flow chamber 16 is located at a predetermined position along intermediate section 14 of conduit 9. Conduit 9 then exits the enclosure at exit section 18. It is preferred that conduit 9 be securely mounted to enclosure 4, primarily in order to ensure that flow chamber 16 remains stable.

Flow chamber 16 is preferably cylindrical, however it may be of any configuration which allows the passage of the liquid or slurry to be monitored to flow freely therethrough while also accommodating a probe sensor body 20 being secured by a threaded lock ring 21. Flexible electrical lead 24 provides a communication link between a sensor (not shown in FIG. 1) mounted within probe sensor body 20 and a processor means 26. The particular probe sensor body shown in FIG. 1 is designed to hold a sensor for determining the pH of a fluid or slurry. Probe body 20, of which a front view thereof is provided in FIG. 3A of the drawings, is produced by Johnson Yokogawa Corporation, and is commercially available through Applied Control Technology, 1348 E. 35th St., Tulsa, Okla. 74105. As can be seen in FIGS. 3A and 3B, body 20 is cylindrically-shaped and terminates into a sensor portion 62. Sensor portion 62 retains a sensor element 60 which, in conjunction with processor 26, senses the pH of a fluid or slurry upon being submerged therein. In the preferred embodiment shown in FIGS. 3A and 3B of the drawings, sensor element 60 is integral to probe sensor 20. However, a probe sensor having a removable sensor element are commercially available or could be devised if desired.

Probe sensor retainer 66, shown in FIG. 4A and 4B, serves to secure probe sensor body 20 into flow chamber 16 upon installing threaded lock ring 21 about shoulder 72 and flange 70 onto the open end of flow chamber 16. Threaded region 68 of retainer 66 accommodates threaded region 64 of probe sensor 20 shown in FIG. 3B. Retainer 66 can be provided with flat regions 74 for accepting a spanner wrench for tightening purposes. Sensor shield 76 preferably has a curved periphery and extends axially outward from retainer 66 to provide a means of shielding sensor portion 62 from abrasives that may be within the fluid or slurry being monitored. Care should be taken to ensure that shield 76 is provided with enough clearance from sensor portion 62 to prevent the accumulation, or packing, of particles about the sensor thereby isolating a portion of the sensor from the fluid flowing through the chamber. Orientation slot 78 provides a means for identifying and correctly positioning probe sensor 20 within flow chamber 16 so that shield 76 is placed between the incoming fluid and sensor portion 62. Retainer 66, including integral shield 76, are made of 316 L stainless steel, however, any material having suitable characteristics may be employed.

Returning to FIG. 1 of the drawings. Electrical lead 24 is connected to a processor means 26 which converts a signal received from sensor probe 20 into a meaningful value that can be displayed and/or recorded for both process control and data acquisition purposes. The particular processor means shown in FIG. 1 is produced by Johnson Yokogawa Corp., model #EXA PH200 and is also commercially available from Applied Control Technology. Processor 26 is shown being powered by a transformer 30. This allows the processor to be powered by an external power supply having a different voltage than the voltage required by processor 26. Additionally, an external charting device for providing a historical record of the particular value being measured (not shown in the drawings) can be employed if desired.

A calibration reservoir 32, having a removable cap 34, is preferably positioned in close proximity of flow chamber 16, or at least within such distance that probe sensor 20 can be installed therein without over extending lead 24. Such an arrangement is shown in FIG. 2 of the drawings. Referring to either FIG. 1 or FIG. 2, calibration reservoir 32 is provided with a valve 36 for controlling the introduction of preselected calibration and/or storage fluids into and out of reservoir 32. Removable or disposable calibration/storage fluid containers 38 and 40 are positioned above reservoir 32 and are fluidly connected to appropriate inlets of valve 36 via respective lines 42 and 44. Intermediate in-line shut off valves 46 and 48 allow convenient replacement of containers 38 and 40. Brackets 39 and 41 serve to secure and protect containers 38 and 40. Selector 50 controls which fluid from container 38 and 40 will be introduced to reservoir 36. Selector 50 may also be appropriately positioned to allow the draining of fluid from reservoir 36 through drain line 52 which directs the drained fluid out of enclosure 4. Appropriately sized and configured vent line 54 allows reservoir 32 to be filled while minimizing fluid evaporation from within reservoir 32. In the preferred embodiment, vent tube 54 is in fluid connection with an internal passage within the side walls of calibration reservoir 32. As with drain line 52, vent tube 54 directs fluid away from enclosure 4.

Although the apparatus depicted within the drawings has two calibration/storage solution containers and an appropriate reservoir control valve, a lesser or greater number of such calibration/storage solution containers and a reservoir control valve having the appropriate number of ports can be provided to suit particular applications of the disclosed invention. For example, no calibration/storage solution containers need be provided in a case where a given amount of a particular fluid placed in the calibration chamber is sufficient for calibration and storage purposes and the benefits of having a readily available supply of a variety of solutions on hand is not needed.

OPERATION OF THE INVENTION

As the preferred embodiment of the present invention shown in the drawings is particularly suited to the measurement of the pH of a fluid, or slurry, the operation of the present invention will therefore be discussed with respect to such an application. Referring now to FIG. 2 of the drawings. After apparatus 2 is secured at the job site, fluid or slurry to be monitored is routed through conduit 9 by way of conventional plumbing or flexible hoses.

Containers 38 and 40 having solutions of known pH values are placed in their respective locations and secured by brackets 38 and 40 if not done so previously. Typically, one container has a probe calibration/soaking solution having a neutral pH of 7.0, and the other container has a calibration solution having a pH of 4.0 or 10.0. The containers are respectively attached to reservoir feed lines 42 and 44 and valves 46 and 48 are opened after checking that selector 50 of reservoir control valve 36 is in the all ports closed position.

Shut-off valve 12 is closed and probe sensor 20, having pH sensor 62 previously installed thereon, is positioned and secured within calibration reservoir 32 by lock ring 21. Processor 26 is energized by internal power supply 30 or by an external power supply.

Calibration fluid is introduced into calibration reservoir 32 by selecting the appropriate position on control valve selector 50. Air displaced by entering fluid is vented to atmosphere by way of vent tube 54. Upon reservoir 32 being filled to the desired level, namely a level that ensures sensor portion 62 is completely submerged which is indicated by fluid flowing out of vent tube 54. The selector valve is then rotated to the all ports closed position. Sensor portion 62 being surrounded by the calibration fluid causes processor 26 to display or otherwise indicate the pH of the calibration solution. The processor is tuned until the known pH of the calibration fluid is displayed. After the indicated value is stable, the calibration solution is evacuated from reservoir 32 by rotating selector 50 to the drain position whereupon, the solution exits the reservoir through drain line 52. After drainage is complete, selector 50 is rotated to allow the second calibration/storage solution into the reservoir. After the reservoir is adequately filled, the valve is rotated to the all ports closed position and the value of the pH is observed and processor 26 again tuned to display the known pH value of the second solution. The second solution can then be drained if desired and the reservoir refilled with the first solution and the calibration steps repeated with the two solutions until the operator is satisfied that the probe sensor is properly calibrated.

Upon completion of the calibration procedure, the now calibrated probe sensor 20 may be removed from reservoir 32, installed in flow chamber 16 and secured by lock ring 21. Shut-off valve 12 may be opened to allow the fluid or slurry to flow through flow chamber 16 thereby submerging sensor portion 62 of probe sensor 20 which causes processor 26 to display and/or record the pH value of the fluid passing through flow chamber 16. Shut-off valve 12 may also be used as a throttle valve if the flow rate of the fluid proves to be excessive during the monitoring process.

Should the operator desire to check or confirm that the processor and probe sensor is calibrated during the monitoring process, shut-off valve 12 is closed and probe sensor 20 removed from flow chamber 16 and reinstalled in calibration chamber 32 where the calibration thereof can be verified, or reset if necessary. Alternatively, a replacement probe sensor can be calibrated prior to removing the first probe from flow chamber 16 and installing the replacement probe sensor in its place. Furthermore, multiple flow chambers and calibration chambers, or flow chambers and calibration chambers configured to accommodate more than one sensor probe at a time can be provided to minimize the amount of time that the fluid or slurry is not being monitored due to re-calibration or replacement thereof.

Upon completion of the monitoring process, probe sensor 20 is installed in calibration chamber 32 and the chamber is filled with storage solution, which is typically the calibration solution having a pH of 7.0, 4.0 or 3.0, by rotating control valve 50 to the proper position. After calibration reservoir 32 is filled, control valve 50 is turned to the all ports off position and the probe sensor will remain hydrated as well as be protected until the next monitoring or measuring process is undertaken.

As will be apparent to those skilled in the art, the preferred embodiment is well adapted for the monitoring or measurement of pH values of fluids or slurries in hostile environments. It is further apparent that the disclosed invention can readily be adapted to measure or monitor other attributes of fluids, slurries, or other media, and all such adaptations are encompassed within the scope and spirit of the following claims.

What is claimed is:

1. A measurement, calibration and probe storage apparatus for use in connection with the protection of oil and gas comprising:
    a) a rigid, protective, mountable, enclosure having a conduit means routed therethrough for the conveyance of at least one of a fluid, a slurry and mixture thereof;
    b) a cylindrical flow chamber being configured to accommodate a removable probe sensor means therein and a removable dust cap thereon, the flow chamber being in fluid communication with the conduit;
    c) at least one removable dip probe sensor means for measuring a preselected attribute of said at least one of a fluid, a slurry, and mixture thereof, in which the probe sensor is immersed;
    d) an electronic processor means in electrical communication with the probe sensor for calculating and rendering a value of the attribute being measured;
    e) a cylindrical probe sensor storage and calibration chamber being proximal to the flow chamber, adapted to accommodate the removable probe sensor therein and a removable dust cap thereon, the storage and calibration chamber further having a drain tube and an overfill tube, both being in fluid communication with the storage and calibration chamber, the drain tube being selectively controlled by a multi-position control valve means;
    f) a dust cap being configured to be accommodated by the flow chamber and the storage and calibration chamber; and
    g) a control valve means for selectively controlling the filling of the storage and calibration chamber from at least one calibration fluid reservoir, and for the draining of the calibration chamber.

2. The apparatus of claim 1 further comprising a removable protective shield adapted to be fitted on a predetermined section of the probe sensor for protecting the sensor mounted within the sensor probe from abrasives contained within a fluid, or slurry, being monitored.

3. The apparatus of claim 1 further comprising a shut off valve being positioned in the conduit up stream of the flow chamber.

4. The apparatus of claim 1 wherein the enclosure is rectangularly shaped, has a front access panel, and has mounting tabs extending from the periphery of the enclosure at preselected locations.

5. The apparatus of claim 1 wherein the attribute being measured in the pH of a calibration liquid, or a process liquid or slurry.

6. The apparatus of claim 1 wherein said at least one calibration liquid reservoir is provided with a tubing means fluidly connecting said at least one calibration liquid reservoir with the multi-posit on control valve means and wherein each tubing means includes an in-line shut off valve.

7. The apparatus of claim 1 wherein the removable probe sensor, the storage and calibration chamber, the removable dust caps and the flow chamber have complementary threaded lock means for interchangeably engaging the probe sensor and dust caps about the flow chamber and the storage and calibration chamber.

8. The apparatus of claim 1 wherein the electrical processing means includes output means for recording measurements and includes an input connection for connection auxiliary power means.

9. The apparatus of claim 1 wherein the protective enclosure is rectangularly-shaped, has mounting tabs, has a front access panel, and is constructed of steel.

10. A pH measurement, calibration and probe storage apparatus for use in connection with the production of oil and gas comprising:

a) a protective, mountable, steel rectangular enclosure having mounting tabs and a front access panel and having a conduit means routed therethrough for the conveyance of at least one of a fluid, a slurry, and mixture thereof;

b) a cylindrical flow chamber being configured to accommodate a removable probe sensor means therein and a removable dust cap thereon, the flow chamber being in fluid communication with the conduit;

c) a shut-off valve being located in the conduit means upstream of the flow chamber;

d) at least one removable dip probe sensor means for measuring the pH of at least one of a fluid, a slurry, and mixture thereof, in which the probe sensor is immersed, and the probe sensor means being provided with a means for shielding the probe sensor from particles and abrasives that may be present within the at least one of a fluid, a slurry, and mixture thereof, being measured;

e) an electronic processor means in electrical communication with the probe sensor for calculating and rendering a value of the attribute being measured and the electrical processing means including an output means for recording measurements and including an input connection for connecting auxiliary power means;

f) a cylindrical probe sensor storage and calibration chamber being adapted to accommodate the removable probe sensor therein and a removable dust cap thereon, the storage and calibration chamber further having a drain tube and an overfill tube, both being in fluid communication with the storage and calibration chamber, the drain tube being selectively controlled by a multi-position control valve means;

g) a dust cap being configured to be accommodated by the flow chamber and the storage and calibration chamber; and h) a multi-position control valve means for selectively controlling the filling of the storage and calibration chamber from at least two calibration fluid reservoirs, and for the draining of the calibration chamber.

11. The apparatus of claim 10 wherein each calibration liquid reservoir is provided with a means for fluidly connecting each calibration liquid reservoir with the multi-position control valve means and wherein each fluid connection means includes an in-line shut off valve.

12. The apparatus of claim 10 wherein the removable probe sensor, the storage and calibration chamber, the removable dust caps and the flow chamber have complementary threaded lock means for interchangeable engaging the probe sensor and dust caps about the flow chamber and the storage and calibration chamber.

* * * * *